(12) United States Patent
Seow et al.

(10) Patent No.: US 10,869,729 B2
(45) Date of Patent: Dec. 22, 2020

(54) ROBOTIC SURGICAL ASSEMBLIES (71) Applicant: Covidien LP, Mansfield, MA (US)

(72) Inventors: Chi Min Seow, New Haven, CT (US); Jaimeen Kapadia, Cambridge, MA (US); Mark Macleod, Southbury, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 299 days.

(21) Appl. No.: 16/081,335

(22) PCT Filed: Feb. 27, 2017

(86) PCT No.: PCT/US2017/019584
§ 371 (c)(1),
(2) Date: Aug. 30, 2018

(87) PCT Pub. No.: WO2017/151458
PCT Pub. Date: Sep. 8, 2017

(65) Prior Publication Data
US 2019/0021803 A1    Jan. 24, 2019

Related U.S. Application Data (60) Provisional application No. 62/303,574, filed on Mar. 4, 2016.

(51) Int. Cl.
*A61B 34/30* (2016.01)
*A61B 34/35* (2016.01)
(Continued)

(52) U.S. Cl.
CPC .............. *A61B 34/35* (2016.02); *A61B 34/30* (2016.02); *A61B 90/03* (2016.02);
(Continued)

(58) Field of Classification Search
CPC ...... A61B 2017/3409; A61B 2034/301; A61B 2090/035; A61B 34/30; A61B 34/35
See application file for complete search history.

(56) References Cited

U.S. PATENT DOCUMENTS

| 3,388,847 A | 6/1968 | Kasulin et al. |
| 3,552,626 A | 1/1971 | Astafiev et al. |

(Continued)

FOREIGN PATENT DOCUMENTS

| CA | 908529 A | 8/1972 |
| CA | 1136020 A1 | 11/1982 |

(Continued)

OTHER PUBLICATIONS

European Search Report, dated Apr. 28, 2016, corresponding to European Application No. 15195534.1; 10 pages.

(Continued)

*Primary Examiner* — Ryan J. Severson
(74) *Attorney, Agent, or Firm* — Carter, DeLuca & Farrell LLP (57) ABSTRACT

An instrument drive unit includes a hub, a motor pack, and an annular member disposed between the hub and the motor pack. The hub and motor pack each have a surface feature. The motor pack is rotatably coupled to the hub. The annular member defines an upper annular channel, and a lower annular channel. The annular member has a stop formed in each of the upper and lower annular channels. Upon the motor pack achieving a threshold amount of rotation relative to the hub, the surface feature of the motor pack abuts the stop of the lower annular channel to rotate the annular member. Upon the annular member achieving a threshold amount of rotation relative to the hub, the stop of the upper annular channel abuts the surface feature of the hub stopping further rotation of the motor pack.

20 Claims, 8 Drawing Sheets

(51) Int. Cl.
*A61B 90/00* (2016.01)
*A61B 17/00* (2006.01)
*A61B 17/34* (2006.01)

(52) U.S. Cl.
CPC .............. *A61B 2017/00477* (2013.01); *A61B 2017/3409* (2013.01); *A61B 2090/035* (2016.02); *A61B 2090/067* (2016.02)

(56) References Cited

U.S. PATENT DOCUMENTS

| | | |
|---|---|---|
| 3,638,652 A | 2/1972 | Kelley |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,595,887 B2 | 7/2003 | Thoma |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |

(56) References Cited

U.S. PATENT DOCUMENTS

| | | |
|---|---|---|
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,659,939 B2 * | 12/2003 | Moll ............... A61B 34/30 |
| | | 600/102 |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,763,993 B2 | 7/2004 | Bolduc et al. |
| 6,769,590 B2 | 8/2004 | Vresh et al. |
| 6,945,444 B2 | 9/2005 | Gresham et al. |
| 6,959,851 B2 | 11/2005 | Heinrich |
| 7,059,331 B2 | 6/2006 | Adams et al. |
| 7,063,095 B2 | 6/2006 | Barcay et al. |
| 7,168,604 B2 | 1/2007 | Milliman et al. |
| 7,204,844 B2 | 4/2007 | Jensen et al. |
| 7,303,106 B2 | 12/2007 | Milliman et al. |
| 7,325,713 B2 | 2/2008 | Aranyi |
| RE40,237 E | 4/2008 | Bilotti et al. |
| 7,357,774 B2 * | 4/2008 | Cooper ............... A61B 46/13 |
| | | 600/102 |
| 7,364,060 B2 | 4/2008 | Milliman |
| 7,399,305 B2 | 7/2008 | Csiky et al. |
| 7,401,722 B2 | 7/2008 | Hur |
| 7,407,075 B2 | 8/2008 | Holsten et al. |
| 7,802,712 B2 | 9/2010 | Milliman et al. |
| 8,517,241 B2 | 8/2013 | Nicholas et al. |
| 9,724,163 B2 * | 8/2017 | Orban ............... A61B 46/10 |
| 10,271,911 B2 * | 4/2019 | Cooper ............... A61B 34/70 |
| 10,307,213 B2 * | 6/2019 | Holop ............... A61B 34/30 |
| 10,321,964 B2 * | 6/2019 | Grover ............. A61B 17/32002 |
| 10,595,945 B2 * | 3/2020 | Kapadia ........... A61B 17/00234 |
| 10,631,949 B2 * | 4/2020 | Schuh ............... A61B 46/10 |
| 10,675,104 B2 * | 6/2020 | Kapadia ............. A61B 17/29 |
| 10,736,219 B2 * | 8/2020 | Seow ............... H05K 1/028 |
| 2003/0013949 A1 * | 1/2003 | Moll ............... G09B 23/285 |
| | | 600/407 |
| 2003/0225411 A1 | 12/2003 | Miller |
| 2011/0015650 A1 * | 1/2011 | Choi ............... A61B 34/30 |
| | | 606/130 |
| 2012/0116416 A1 | 5/2012 | Neff et al. |
| 2015/0173841 A1 | 6/2015 | Orban |
| 2019/0021803 A1 * | 1/2019 | Seow ............... A61B 34/35 |

FOREIGN PATENT DOCUMENTS

| | | |
|---|---|---|
| DE | 1057729 B | 5/1959 |
| DE | 19510707 A1 | 9/1996 |
| DE | 102005048211 A1 | 4/2007 |
| DE | 102010008745 A1 | 8/2011 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 2105106 A1 | 9/2009 |
| FR | 1136020 A | 5/1957 |
| FR | 1461464 A | 2/1966 |
| FR | 1588250 A | 4/1970 |
| WO | 01/51116 A2 | 7/2001 |

OTHER PUBLICATIONS

European Communication dated Feb. 16, 2017, corresponding to European Application No. 15 195 534.1; 4 pages.
European partial supplementary Search Report, dated Oct. 17, 2019, corresponding to European Application No. 17760519.3; 12 pages.
Chinese Office Action dated Oct. 23, 2020, issued in corresponding Chinese Appln. No. 201780013436, 10 pages.

* cited by examiner

ROBOTIC SURGICAL ASSEMBLIES

CROSS-REFERENCE TO RELATED APPLICATIONS

This application is a U.S. National Stage Application filed under 35 U.S.C. § 371(a) of International Patent Application Serial No. PCT/US2017/019584, filed Feb. 27, 2017, which claims the benefit of and priority to U.S. Provisional Patent Application Ser. No. 62/303,574, filed Mar. 4, 2016, the entire disclosure of which is incorporated by reference herein.

BACKGROUND

Robotic surgical systems have been used in minimally invasive medical procedures. Some robotic surgical systems included a console supporting a surgical robotic arm and a surgical instrument, having at least one end effector (e.g., forceps or a grasping tool), mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

Typically, an inner component of the instrument drive unit was rotated to rotate the surgical instrument about its longitudinal axis. Making the instrument drive unit rotatable provides for a more simplified surgical instrument including staplers, electrosurgical instruments, and straight instruments. However, there is a limit to the amount the instrument drive unit and surgical instrument can rotate without causing damage to their internal components.

Accordingly, a need exists for a way of either monitoring and/or controlling the amount the instrument drive unit and/or surgical instrument is rotated.

SUMMARY

In accordance with an aspect of the present disclosure, an instrument drive unit for use with a robotic arm is provided. The instrument drive unit includes an outer shell and an inner shell removably received within the outer shell. The outer shell is configured to be selectively coupled to a robotic arm. The inner shell includes a hub, a motor pack, and an annular member. The hub is non-rotatably received within the outer shell and has a distally extending surface feature. The motor pack includes a proximal end rotatably coupled to the hub and a surface feature extending proximally from the proximal end thereof. The annular member defines an upper annular channel and a lower annular channel. The upper annular channel has the surface feature of the hub received therein. The lower annular channel has the surface feature of the motor pack received therein. The annular member has a stop formed in each of the upper and lower annular channels. Upon the motor pack achieving a threshold amount of rotation relative to the hub, the surface feature of the motor pack abuts the stop of the lower annular channel to rotate the annular member relative to the hub. Upon the annular member achieving a threshold amount of rotation relative to the hub, the stop of the upper annular channel abuts the surface feature of the hub stopping further rotation of the motor pack.

In some embodiments, each of the proximal end of the motor pack, the annular member, and the hub may have a sensor in communication with one another and configured to sense the relative rotational positions of one another. The sensor of the motor pack may be disposed adjacent the surface feature thereof. The sensor of the annular member may be disposed adjacent the stop of the upper or lower annular channels. The sensor of the hub may be disposed adjacent the surface feature thereof. The sensors of each of the motor pack, the annular member, and the hub may be hall effect sensors, rotary variable differential transformers, variable reluctance sensors, potentiometers, capacitive rotary position sensors, optical encoders, or laser surface velocimeters.

It is contemplated that the threshold amount of rotation of the motor pack relative to the hub may be approximately 1 to 360 degrees, threshold amount of rotation of the annular member relative to the hub may be approximately 1 to 360 degrees, such that the motor pack is configured to rotate approximately 2 to 720 degrees relative to the outer shell.

It is envisioned that the annular member may be a hollow ring having an H-shaped transverse cross sectional profile.

In some aspects of the present disclosure, the surface feature of the motor pack may be a curved projection slidably received within the lower annular channel of the annular member. The surface feature of the hub may be a curved projection slidably received within the upper annular channel of the annular member.

In another aspect of the present disclosure, a surgical assembly for use with and for selective connection to a robotic arm is provided. The surgical assembly includes an instrument drive unit. The instrument drive unit includes a hub, a motor pack, and an annular member. The hub has a surface feature. The motor pack has a surface feature and is rotatably coupled to the hub. The annular member is disposed between the hub and the motor pack. The annular member defines an upper annular channel and a lower annular channel. The annular member has a stop formed in each of the upper and lower annular channels. Upon the motor pack achieving a threshold amount of rotation relative to the hub, the surface feature of the motor pack abuts the stop of the lower annular channel to rotate the annular member. Upon the annular member achieving a threshold amount of rotation relative to the hub, the stop of the upper annular channel abuts the surface feature of the hub stopping further rotation of the motor pack.

In some embodiments, the instrument drive unit may further include an outer shell. The hub may be non-rotatably received within the outer shell. The surgical assembly may further include a surgical instrument holder that includes a carriage housing and a motor disposed within the carriage housing. The carriage housing may have a first side configured for movable engagement to a surgical robotic arm, and a second side configured for non-rotatably supporting the outer shell of the instrument drive unit. The motor may be configured to effect rotation of the motor pack of the instrument drive unit.

It is envisioned that the surgical instrument holder may further include control circuitry disposed within the carriage housing and in communication with the motor and a sensor of each of the motor pack, the annular member, and the hub. The control circuitry is configured to stop operation of the motor upon the stop of the upper annular channel being disposed adjacent the surface feature of the hub.

It is contemplated that the surface feature of the hub may extend distally from the hub, and the surface feature of the motor pack may extend proximally from the proximal end thereof. The motor pack may have a proximal end rotatably coupled to the hub.

In some aspects of the present disclosure, the motor pack may have a distal end configured to be non-rotatably coupled to a proximal end of an electromechanical instrument. The motor pack of the instrument drive unit may be configured to actuate functions of the electromechanical instrument. The electromechanical instrument may rotate with rotation of the motor pack of the instrument drive unit.

In yet another aspect of the present disclosure, an instrument drive unit for use with a robotic arm is provided and includes an outer shell configured to be coupled to a robotic arm, a drive motor, an interface, and a drive motor output. The drive motor is selectively moveable in an orbit within the outer shell around a central axis. The interface is coupled to the outer shell and configured to be selectively couplable to a surgical instrument. The drive motor output is coupled to the drive motor and configured to be coupled to an input of a surgical instrument when the interface is coupled to an interface of a surgical instrument.

In some embodiments, the drive motor may be encased within the outer shell.

It is contemplated that the outer shell may remain stationary when the drive motor is selectively moved in the orbit. The drive motor may be a plurality of drive motors selectively movable as a group in the orbit within the outer shell. Each of the drive motors may have a drive motor output configured to be coupled to a respective input of a surgical instrument. The instrument drive unit may be configured to rotate the surgical instrument about the central axis when the interface of the instrument drive unit is selectively coupled to an interface of the surgical instrument.

It is envisioned that the instrument drive unit may further include an electro-mechanical actuator coupled to at least one of the drive motors. The electro-mechanical actuator is configured to rotate the surgical instrument about the central axis while moving the drive motors, the drive motor outputs, and the respective inputs of the surgical instrument in the orbit within the outer shell when the interface of the surgical instrument is selectively coupled to the interface of the instrument drive unit.

In yet another aspect of the present disclosure, another embodiment of an instrument drive unit for use with a robotic arm is provided. The instrument drive unit includes an outer shell configured to be selectively coupled to a robotic arm, and an inner shell removably received within the outer shell. The inner shell includes a hub, a motor pack, and first and second annular members. The hub is non-rotatably received within the outer shell and has a distally extending surface feature. The motor pack includes a proximal end rotatably coupled to the hub, and a surface feature extending proximally from the proximal end thereof. The first annular member defines an upper annular channel having the surface feature of the hub received therein. The first annular member has a stop formed in the upper channel thereof. The second annular member is associated with the first annular member and defines a lower annular channel. The second annular member has a stop formed in the lower annular channel thereof. Upon the motor pack achieving a threshold amount of rotation relative to the hub, the surface feature of the motor pack abuts the stop of the lower annular channel of the second annular member to rotate the second annular member relative to the hub. Upon the first annular member achieving a threshold amount of rotation relative to the hub, the stop of the upper annular channel of the first annular member abuts the surface feature of the hub stopping further rotation of the motor pack.

In some embodiments, the instrument drive unit may include a third annular member interposed between the first and second annular members.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical assembly including an instrument drive unit for driving the operation of an electromechanical instrument, a rotational position sensing system, and methods thereof are described in detail with reference to the drawings, in which like reference numerals designate identical or corresponding elements in each of the several views. As used herein the term "distal" refers to that portion of the robotic surgical system, surgical assembly, or component thereof, that is closest to the patient, while the term "proximal" refers to that portion of the robotic surgical system, surgical assembly, or component thereof, further from the patient.

As will be described in detail below, provided is a surgical assembly configured to be attached to a surgical robotic arm. The surgical assembly includes an instrument drive unit configured to rotate a surgical instrument about a longitudinal axis thereof. The instrument drive unit includes a rotational position sensing system configured to determine and regulate the degree of rotation of the surgical instrument about its longitudinal axis.

Figure 1:
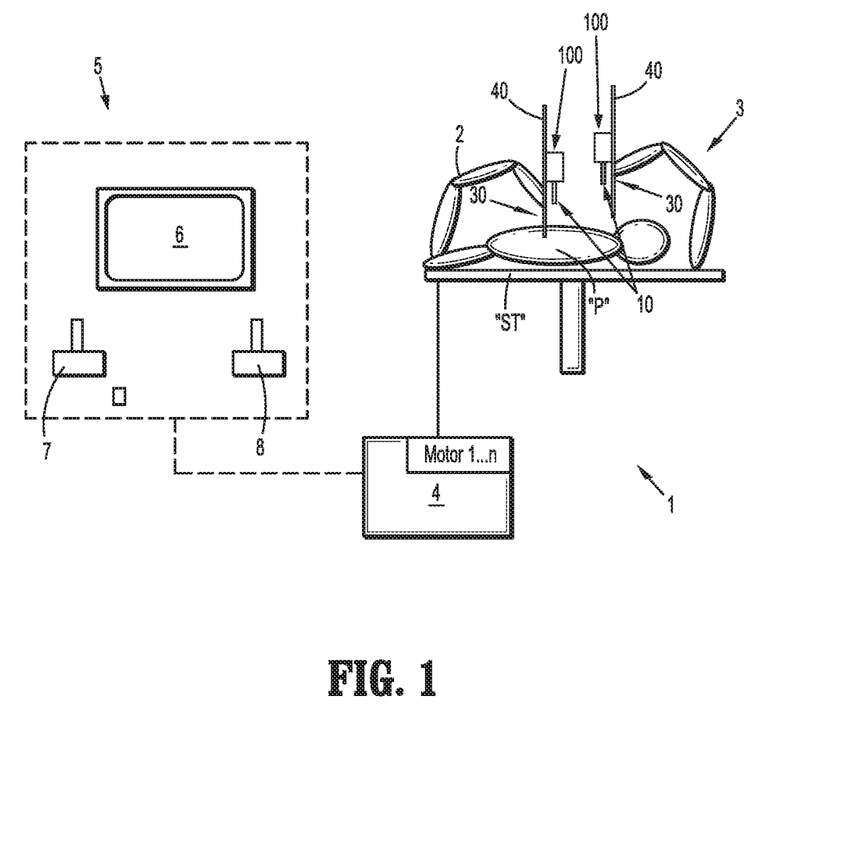
FIG. 1 is a schematic illustration of a robotic surgical system including a surgical assembly in accordance with the present disclosure.
Figure 2A:
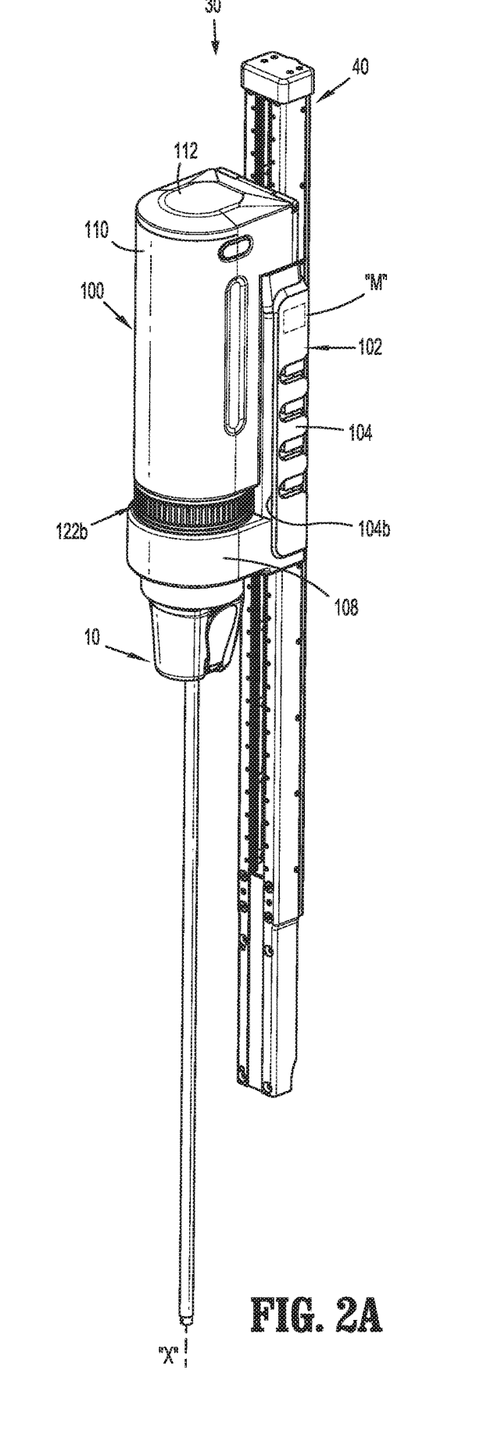
FIG. 2A is a front, perspective view of the surgical assembly of FIG. 1 including a slider, a surgical instrument holder, an instrument drive unit, and a surgical instrument.
Figure 2B:
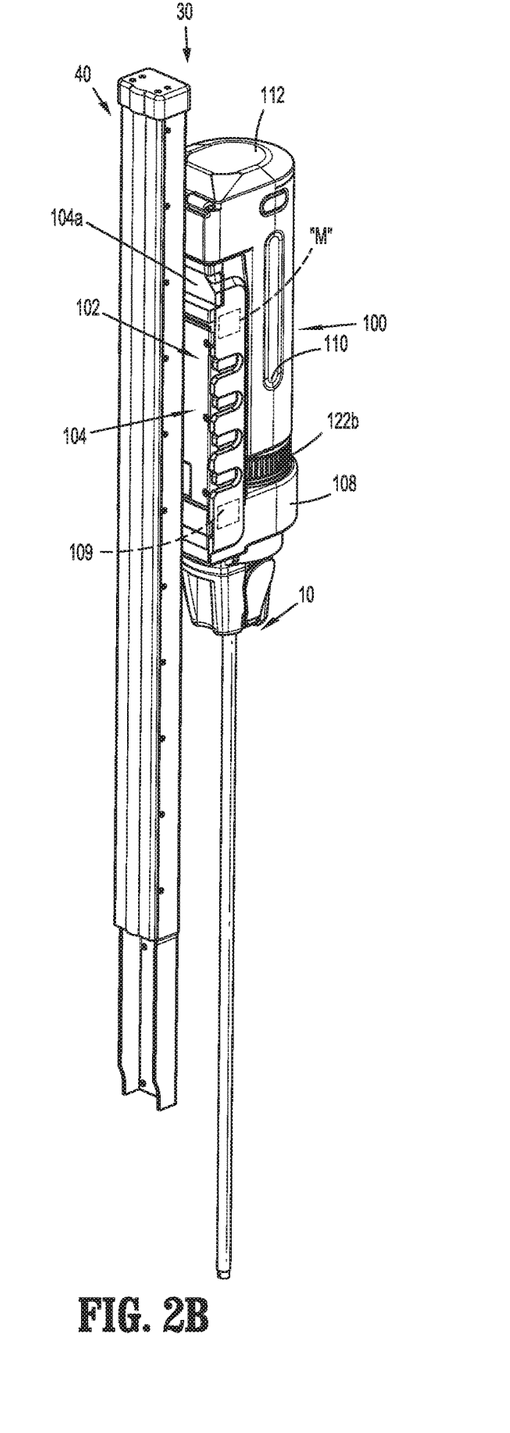
FIG. 2B is a rear, perspective view of the surgical assembly of FIG. 1 including the slider, the surgical instrument holder, the instrument drive unit, and the surgical instrument.

Referring initially to FIGS. 1 and 2, a surgical system, such as, for example, a robotic surgical system 1, generally includes a plurality of surgical robotic arms 2, 3 having an instrument drive unit 100 and an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 100, and thus electromechanical instrument 10 execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 10 (including an electromechanical end effector (not shown)), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a motor pack 122 (FIG. 3) of instrument drive unit 100 to drive various operations of surgical instrument 10, and may control a rotation of motor pack 122 of instrument drive unit 100 to ultimately rotate electromechanical instrument 10 along a longitudinal axis "X" thereof, as will be described in detail below. Motor pack 122 includes a plurality of drive motors 125a, 125b having respective drive motor outputs 127a, 127b configured to be coupled to respective inputs of the surgical instrument 10. In embodiments, each drive motor 125a, 125b of motor pack 122 can be configured to actuate a drive rod or a lever arm to effect operation and/or movement of each electromechanical end effector (not shown) of electromechanical instrument 10. In some embodiments, motor pack 122 of instrument drive unit 100 can be used to drive a lead screw (not explicitly shown) of the electromechanical surgical instrument 10.

For a detailed description of the construction and operation of a robotic surgical system, reference may be made to U.S. Patent Application Publication No. 2012/0116416, filed on Nov. 3, 2011, entitled "Medical Workstation," the entire contents of which are incorporated by reference herein.

With continued reference to FIGS. 1 and 2, robotic surgical system 1 includes a surgical assembly 30, which includes surgical instrument holder 102 coupled with or to robotic arm 2, the instrument drive unit 100 coupled to surgical instrument holder 102, and the electromechanical instrument 10 coupled to instrument drive unit 100. Surgical instrument holder 102 of surgical assembly 30 holds instrument drive unit 100 and surgical instrument 10 and operably couples instrument drive unit 100 to robotic arm 2. Surgical instrument holder 102 includes an interface panel or carriage 104 and an outer housing portion 108 extending perpendicularly from an end of carriage 104. Carriage 104 supports or houses a motor "M," which receives controls and power from control device 4. Carriage 104 has a first side 104a, and a second side 104b. First side 104a of carriage 104 is slidably mounted onto a rail 40 of robotic arm 2. Carriage 104 may be moved along rail 40 via a motor driven chain or belt (not shown) or the like. Second side 104b of carriage 104 of surgical instrument holder 102 is configured for non-rotatable attachment of an outer shell 110 of instrument drive unit 100.

Outer housing portion 108 of surgical instrument holder 102 defines a passageway (not shown) therethrough configured to receive a distal end or interface 122b of a motor pack 122 of instrument drive unit 100. As such, when instrument drive unit 100 is attached to surgical instrument holder 102, outer shell 110 of instrument drive unit 100 is non-rotatably connected to second side 104b of carriage 104, and distal end or interface 122b of motor pack 122 of instrument drive unit 100 is rotatably received within the passageway of outer housing portion 108 of surgical instrument holder 102.

Surgical instrument holder 102 further includes control circuitry 109 disposed within carriage 104. Control circuitry 109 is in communication with an electro-mechanical actuator, such as, for example, a motor "M" to control the operation of motor "M." Motor "M" is configured to be operably coupled to motor pack 122 of instrument drive unit 100 to drive a rotation of motor pack 122. In some embodiments, control circuitry 109 may be disposed within any of the components of surgical assembly 30.

Figure 3:
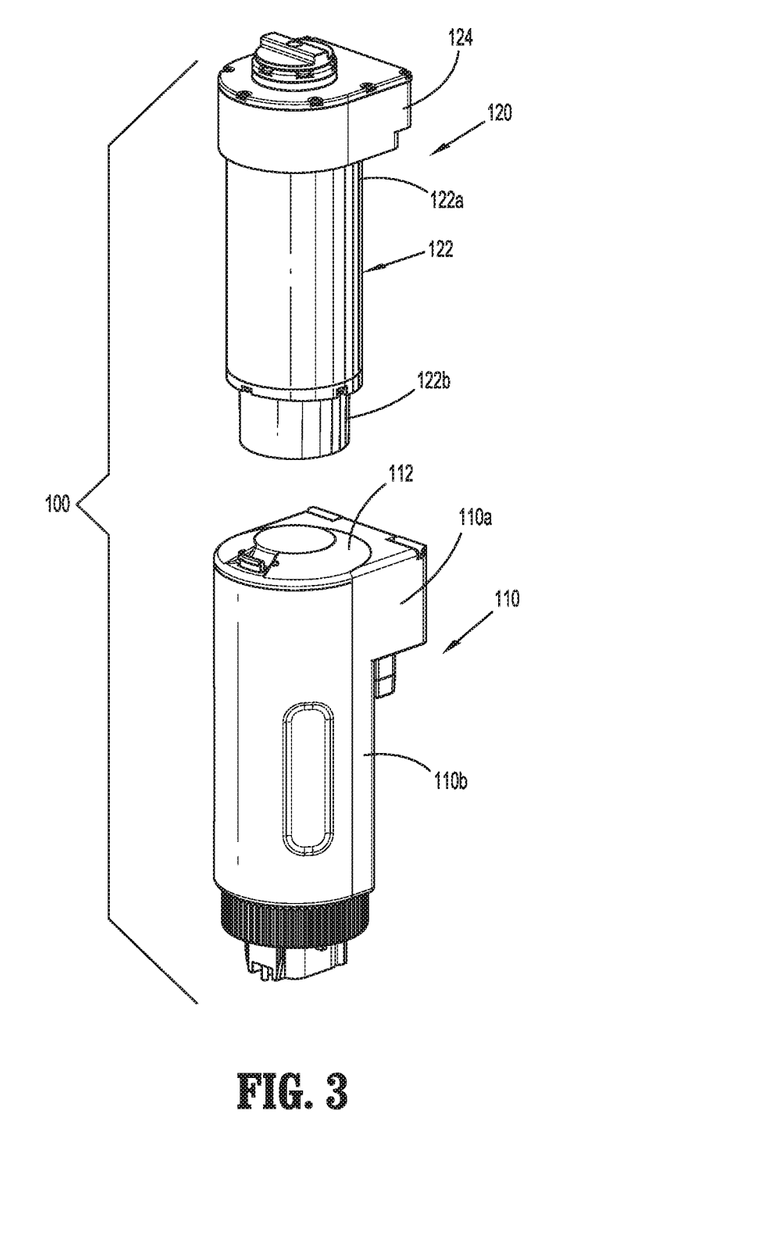
FIG. 3 is a perspective view of the instrument drive unit of FIG. 1 including an outer shell and an inner shell.
Figure 4:
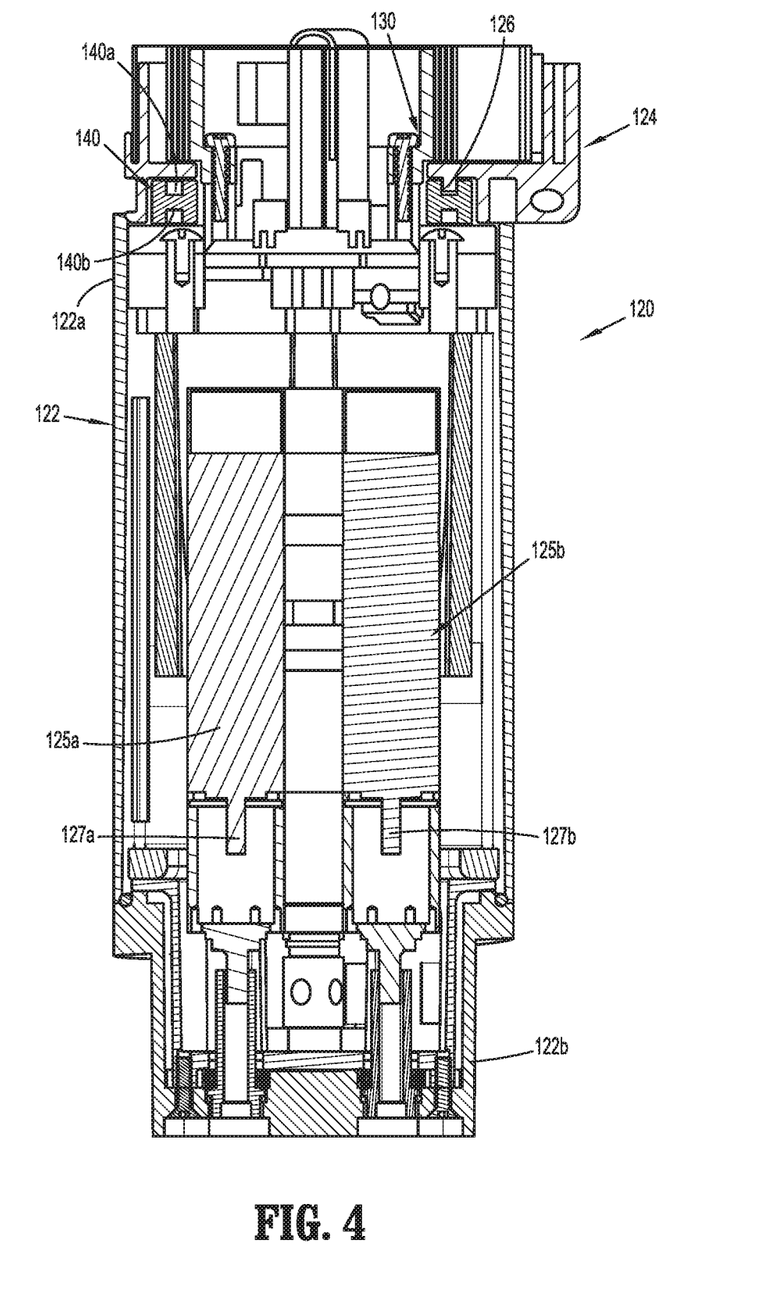
FIG. 4 is a longitudinal cross-sectional view of the instrument drive unit of FIG. 3 including a rotational position sensing system, according to an embodiment of the present disclosure.

With reference to FIGS. 3 and 4, instrument drive unit 100 transfers power and actuation forces from its motors (FIG. 4) to driven members (not shown) of electromechanical instrument 10 (FIG. 2) to ultimately drive movement of components of the end effector (not shown) of electromechanical instrument 10, for example, a movement of a knife blade (not shown) and/or a closing and opening of jaw members (not shown) of the end effector. Instrument drive unit 100 generally includes an outer shell 110 and an inner shell 120 disposed within outer shell 110.

Outer shell 110 of instrument drive unit 100 encloses the inner components of instrument drive unit 100 to form a sterile barrier between an interior of instrument drive unit 100 and the external environment. Outer shell 110 may be disposable, re-usable (upon sterilization), and/or transparent. Outer shell 110 defines a cavity (not shown) therein for removable receipt of inner shell 120 of instrument drive unit 100. Outer shell has a generally U-shaped portion 110a and a cylindrical body 110b extending distally from U-shaped portion 110a. U-shaped portion 110a of outer shell 110 has a lid 112 that is selectively opened during removal or insertion of inner shell 120 within outer shell 110.

Inner shell 120 of instrument drive unit 100 is removably receivable within outer shell 110 of instrument drive unit 100. Inner shell 120 of instrument drive unit 100 includes a hub 124 and a motor pack 122 rotatably coupled to hub 124 and extending distally therefrom. Hub 124 of inner shell 120 has a shape corresponding to U-shaped portion 110a of outer shell 110 such that hub 124 is non-rotatably received within U-shaped portion 110a of outer shell 110. Hub 124 of inner shell 120 has a surface feature 126 extending distally from a distal end thereof. Surface feature 126 is fixed to hub 124 and is slidably received within an upper channel 140a of an annular member 140, as will be described in detail below. Surface feature 126 is a curved projection, but it is contemplated that surface feature 126 may be a tab or a block assuming a variety of shapes, such as, for example, triangular, arcuate, polygonal, uniform, non-uniform, tapered, or the like.

Hub 124 of inner shell 120 of instrument drive unit 100 further includes a sensor s126 (FIG. 5) disposed adjacent to or on surface feature 126 thereof. Sensor s126 of hub 124 is in communication with control circuitry 109 (FIG. 2) of surgical instrument holder 102 to communicate its location to control circuitry 109, as will be described in detail below.

With continued reference to FIGS. 3 and 4, motor pack 122 of inner shell 120 of instrument drive unit 100 has a shape corresponding to cylindrical body 110b of outer shell 110 of instrument drive unit 100 such that motor pack 122 is rotatably receivable within cylindrical body 110b of outer shell 110 of instrument drive unit 100. Motor pack 122 of inner shell 120 has a proximal end 122a that is rotatably coupled to hub 124 of inner shell 110. Motor pack 122 has a surface feature 128 (FIG. 5) extending proximally from proximal end 122a thereof. Surface feature 128 of motor pack 122 is fixed to the proximal end 122a thereof and is slidably received within a lower channel 140b of annular member 140. Surface feature 128 of motor pack 122 is a curved projection, but it is contemplated that surface feature 128 may be a tab or a block assuming a variety of shapes, such as, for example, triangular, arcuate, polygonal, uniform, non-uniform, tapered, or the like.

Motor pack 122 further includes a sensor s122 (FIG. 5) disposed adjacent to or on surface feature 128 thereof. Sensor s122 of motor pack 122 is in communication with control circuitry 109 (FIG. 2) of surgical instrument holder 102 and sensor s126 of hub 124 to communicate its location (e.g., angular location) relative to sensor s126 of hub 124 to control circuitry 109.

Motor pack 122 is operably coupled to motor "M" (FIG. 2) of surgical instrument holder 102 by any suitable drive mechanism, for example, a pulley system. As such, motor pack 122 of inner shell 120 is rotated within outer shell 110 and relative to hub 124 of inner shell 120 via actuation of motor "M" of surgical instrument holder 102. Motor pack 122 may include four motors arranged in a rectangular formation such that respective drive shafts (not shown) thereof are all parallel to one another and all extending in a common direction. The drive shaft of each motor may operatively interface with a respective driven shaft of surgical instrument 10 to independently actuate the driven shafts of surgical instrument 10.

Figure 5:
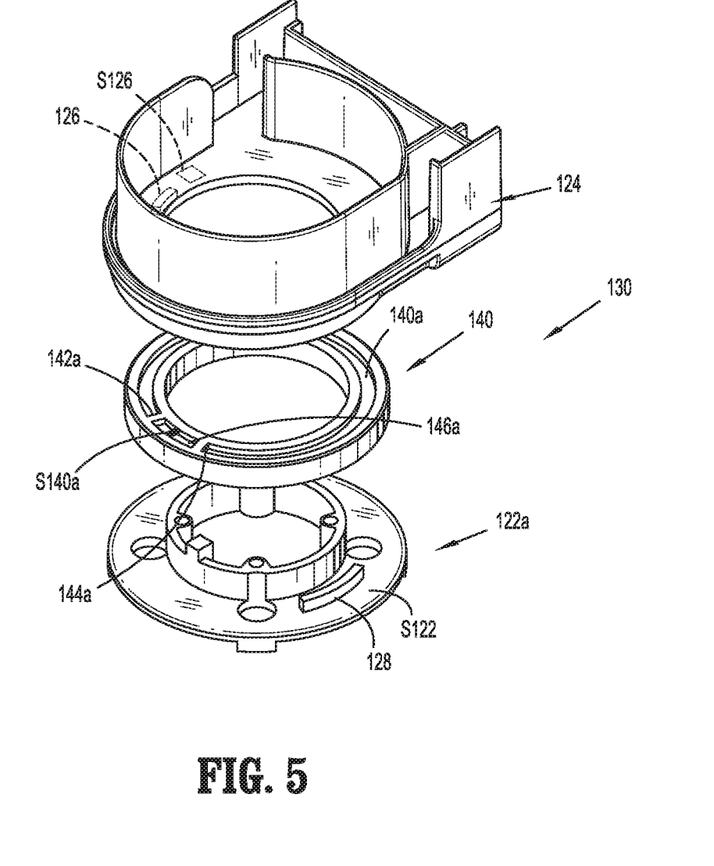
FIG. 5 is a top, perspective view, with parts separated, of the rotational position sensing system of FIG. 4.
Figure 6:
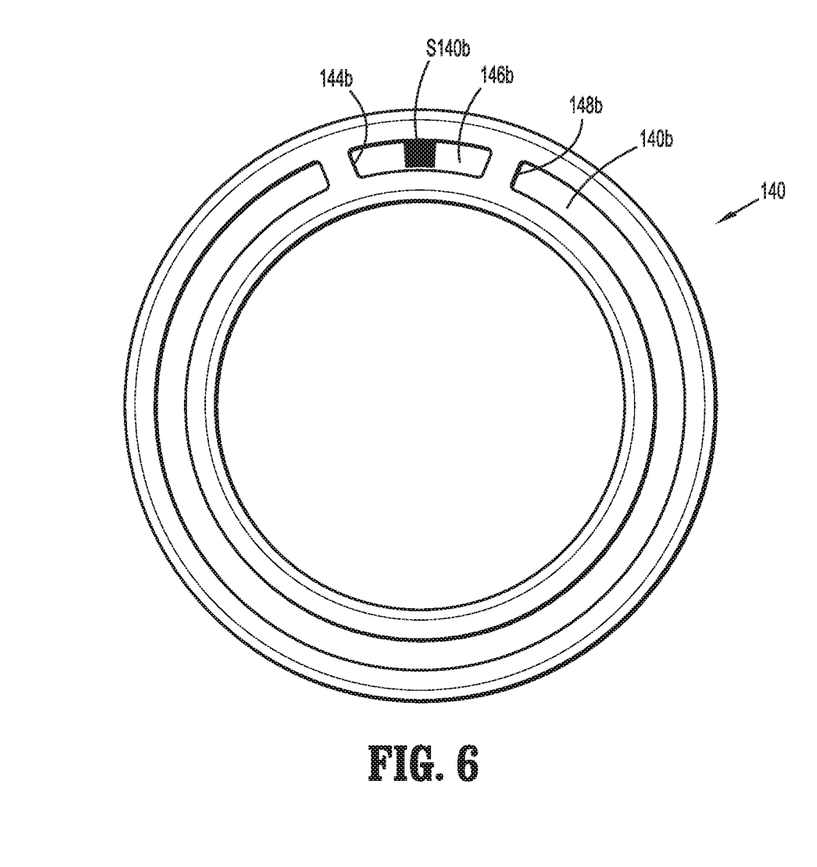
FIG. 6. is a bottom view of an annular member of the rotational position sensing system of FIG. 5.

With reference to FIGS. 4-6, instrument drive unit 100 includes a rotational position sensor system 130 configured to determine and indicate the degree to which motor pack 122, and therefore, surgical instrument 10, rotates about longitudinal axis "X." It is contemplated that sensor system 130 may be configured to calculate/determine and display the amount of revolution(s) of surgical instrument 10 relative to outer shell 110 (FIG. 3) of instrument drive unit 100 about longitudinal axis "X," so that a clinician can determine the precise rotational position of surgical instrument 10 during use thereof.

Sensor system 130 includes the control circuitry 109 (FIG. 2) of surgical instrument holder 102, sensors s126, s122 of hub 124 and motor pack 122, respectively, and an annular member 140. Annular member 140 is rotatably disposed between hub 124 of instrument drive unit 100 and motor pack 122 of instrument drive unit 100. Annular member 140 is a hollow ring, and defines an upper annular channel 140a and a lower annular channel 140b. As such, annular member 140 has an H-shaped transverse cross-sectional profile. Upper annular channel 140a is configured to slidably receive surface feature 126 of hub 124 of instrument drive unit 100 therein. Lower annular channel 140b is configured to slidably receive surface feature 128 of motor pack 122 of instrument drive unit 100 therein. Upper and lower annular channels 140a, 140b each extend along at least a substantial circumference of annular member 140.

Annular member 140 has a first pair of stops 142a, 144a formed in upper annular channel 140a and a second pair of stops 142b, 144b formed in lower annular channel 140b. In some embodiments, instead of annular member 140 having a pair of stops disposed in each channel 140a, 140b, annular member 140 may only have one stop disposed within upper annular channel 140a and one stop disposed within lower annular channel 140b. Stops 142a, 144a, 142b, 144b are generally squared, but may assume a variety of shapes, such as, for example, triangular, arcuate, polygonal, uniform, non-uniform, tapered, or the like. Stops 142a, 144a, 142b, 144b and/or surface features 126, 128 may be fabricated from lubricious (bushing) materials, such as, for example, PEEK, DELRIN, brass, UHMW, or the like.

The second pair of stops 142b, 144b of lower annular channel 140b of annular member 140 are circumferentially aligned (i.e., co-circumferential) with surface feature 128 of motor pack 122 of instrument drive unit 100. As such, upon a threshold amount or degree of rotation (e.g., about 180° to about 360° in a clockwise or counter-clockwise direction) of motor pack 122, surface feature 128 of motor pack 122 abuts or engages one of the second pair of stops 142b, 144b of lower annular channel 140b of annular member 140. In embodiments, the threshold amount of rotation may be about 1° to about 360°. The first pair of stops 142a, 144a of upper annular channel 140a of annular member 140 are circumferentially aligned (i.e., co-circumferential) with surface feature 126 of hub 124 of instrument drive unit 100. As such, upon a threshold amount or degree of rotation (e.g., about 180° to about 360° in a clockwise or counter-clockwise direction) of annular member 140, one of the first pair of stops 142a, 144a of annular member 140 abuts or engages surface feature 126 of hub 124 of instrument drive unit 100 causing rotation of motor pack 122 to stop since hub 124 is rotationally fixed within U-shaped portion 110a of outer shell 110. In embodiments, the threshold amount of rotation may be about 1° to about 360°

The first pair of stops 142a, 144a of upper annular channel 140a are circumferentially spaced from one another to define a gap 146a therebetween. The second pair of stops 142b, 144b of lower annular channel 140b are also circumferentially spaced from one another to define a gap 146b therebetween. Annular member 140 includes a first sensor s140a disposed within gap 146a of upper annular channel 140a, and a second sensor s140b disposed within gap 146b of lower annular member 140b. In some embodiments, sensors s140a, s140b may be positioned at any suitable location on or within annular member 140 that is adjacent respective stops 142a, 144a, 142b, 144b. Sensors s140a, s140b of annular member 140, sensor s126 of hub 124 of instrument drive unit 100, and sensor s122 of motor pack 122 of instrument drive unit 100 are each in communication with one another and with control circuitry 109 (FIG. 2) of surgical instrument holder 102 and are configured to sense the relative rotational or angular positions of one another. Each of sensors s122, s126, s140a, s140b may be hall effect sensors, rotary variable differential transformers, variable reluctance sensors, potentiometers, capacitive rotary position sensors, optical encoders, and/or laser surface velocimeters.

In operation, the rotational position of surgical instrument 10 may be monitored, and/or the rotation of surgical instrument 10 may be stopped, for example, to prevent potential damage to components of surgical assembly 30 from over-rotation of surgical instrument 10. Motor "M" of surgical instrument holder 102 is actuated, which effects a rotation of motor pack 122 of inner shell 120 relative to hub 124 of inner shell 120, in the manner described above. Throughout rotation of motor pack 122, sensor s122 of motor pack 122 and sensor s140b of lower annular channel 140b of annular member 140 sense each other's positions relative to one another and communicate the sensed relative position to control circuitry 109 of surgical instrument holder 102. As such, the rotational position of motor pack 122 and surgical instrument 10 relative to hub 124 is known by control circuitry 109, which may cease actuation of motor "M" when motor pack 122 achieves a preset amount of rotation that is stored in a memory (not shown). Additionally, control circuitry 109 may communicate the known relative rotational position of motor pack 122 from its starting position to display 6 (FIG. 1).

After motor pack 122 achieves a first threshold amount or degree of rotation relative to hub 124 (e.g., about 180° to about 360°), surface feature 128 of motor pack 122 abuts one of the second pair of stops 142b, 144b (depending on the direction of rotation of motor pack 122) of lower annular channel 140b of annular member 140. In embodiments, the threshold amount of rotation may be about 1° to about 360°. Upon the abutment of surface feature 128 of motor pack 122 with one of the second pair of stops 142b, 144b of lower annular channel 140b, continued rotation of motor pack 122 causes annular member 140 to begin rotating.

During rotation of annular member 140 relative to hub 124, sensor s140a of upper annular channel 140a of annular member 140 and sensor s126 of hub 124 sense each other's positions relative to one another and communicate the sensed relative position to control circuitry 109 of surgical instrument holder 102. As such, the rotational position of motor pack 122 and surgical instrument 10 relative to hub 124 is known. After annular member 140 achieves a second threshold amount or degree of rotation relative to hub 124 (e.g., about 180° to about 360°), caused by the continued rotation of motor pack 122, one of the first pair of stops 142a, 144a of upper annular channel 140a of annular member 140 abuts surface feature 126 of hub 124 of instrument drive unit 100 causing annular member 140, and motor pack 122 with surgical instrument 10, to stop rotating. In this way, a continued actuation of "M" of surgical instrument holder 102 will fail to result in a rotation of motor pack 122, thereby preventing any damage from occurring to any components of surgical assembly 30 from the over-rotation of motor pack 122. In embodiments, the threshold amount of rotation may be about 1° to about 360°

A rotation of motor pack 122 in the opposite direction will repeat the process described above until motor pack 122 is prevented from rotating by surface feature 126 of hub 124 of instrument drive unit 100 or another surface feature (not shown) of hub 124 of instrument drive unit 100. It is contemplated that prior to performing a surgical procedure, instrument drive unit 100 may be checked to determine that it is capable of achieving its full rotation in both rotational directions. In particular, motor pack 122 will be rotated in a first direction (e.g., clockwise) until it is stopped, and motor pack 122 will then be rotated in a second direction (e.g., counter-clockwise) until it is stopped. A motor encoder (not shown), e.g., an incremental type, of instrument drive unit 100 may be checked during this process. After motor pack 122 is rotated to its two stopping points, it is repositioned to be between the two stopping points.

It is contemplated that the threshold amount or degree of rotation of motor pack 122 is set based on the position that stops 142a, 144a, 142b, 144b are placed within their respective upper and lower annular channels 140a, 140b. In some embodiments, the threshold amount or degree of rotation may be more or less than 180° or 360° and may be about 360° to about 720°. In embodiments, the threshold amount of rotation may be about 2° to about 720°

It is contemplated, in accordance with an embodiment of the present disclosure, that control circuitry 109 may incorporate a highly toleranced resistor "R" (not shown) with an extremely low resistance, about 0.05 ohms, that is added to a low side of an H-bridge responsible for driving motor "M" of surgical instrument holder 102. In operation, control circuitry 109 measures a voltage "V" drop across resistor "R." By measuring the voltage "V" drop across resistor "R," control circuitry 109 may calculate an amount of current "I" flowing through resistor "R" using Ohm's Law:

$$V=IR$$

In a DC electric motor, which motor "M" may be constructed as, current "I" is directly related to the amount of torque "τ" being developed by using a relation, e.g., the Torque Constant ($K_m$). Accordingly, control circuitry 109 can calculate the amount of torque "τ" being applied to motor "M" according to the following equation:

$$\tau=(K_m)(I)$$

Reference may be made to U.S. Pat. No. 8,517,241, filed on Mar. 3, 2011, for a detailed description of an exemplary embodiment of a control circuitry configured to calculate an amount of torque being applied to motors, the entire contents of which are incorporated by reference herein.

During a normal rotation of surgical instrument 10, a certain or predetermined force profile is expected to be seen by control circuitry 109, e.g., either a current v. time profile (not shown) or a current v. distance profile (not shown). In use, an actuation of motor "M" effects a rotation of motor pack 122 of instrument drive unit 100 as described above. A rotation of motor pack 122 ultimately places surface feature 128 of motor pack 122 into engagement with one of the second pair of stops 142b, 144b of lower annular channel 140b of annular member 140. Upon surface feature 128 of motor pack 122 engaging or coming into contact with one of the second pair of stops 142b, 144b of annular member 140, a static inertia of annular member 140 must be overcome by a certain threshold amount of added torque provided by motor "M." The additional torque required to begin rotating annular member 140 changes a condition of motor "M," which is a change in current "I" delivered to motor "M," which is a different amount of current compared to the expected force profile stored in control circuitry 109.

This increase in current "I" or current spike is registered by control circuitry 109, and control circuitry 109 can reasonably assume that surgical instrument 10 has rotated the threshold amount from its original position. In particular, the current spike indicates that motor pack 122 has rotated a predetermined threshold (e.g., about 180°) from its original rotational position. Since surgical instrument 10 rotates with motor pack 122, the threshold amount of rotation of motor pack 122 registered by control circuitry 109 correlates to the same threshold amount of rotation traveled by surgical instrument 10 about its longitudinal axis "X." Display 6 (FIG. 1) may be provided to indicate, in the form of a number of degrees, the amount of rotation of surgical instrument 10.

Continued rotation of surgical instrument 10 eventually causes one of the first pair of stops 142a, 144a of upper annular channel 140a of annular member 140 to abut or engage surface feature 126 of hub 124, which results in another current spike and an instruction to cease delivering current to motor "M," thereby ceasing rotation of motor pack 122, and therefore rotation of surgical instrument 10. It is envisioned that surface feature 126 of hub 124 may physically resist or prevent further rotation of motor pack 122.

In some embodiments, instrument drive unit 100 may include a single annular member or two or more annular members having any suitable number of variously spaced surface features or tabs. It is further contemplated that the instrument drive unit 100 may include one or more hubs and an annular member corresponding to each hub.

Figure 7:
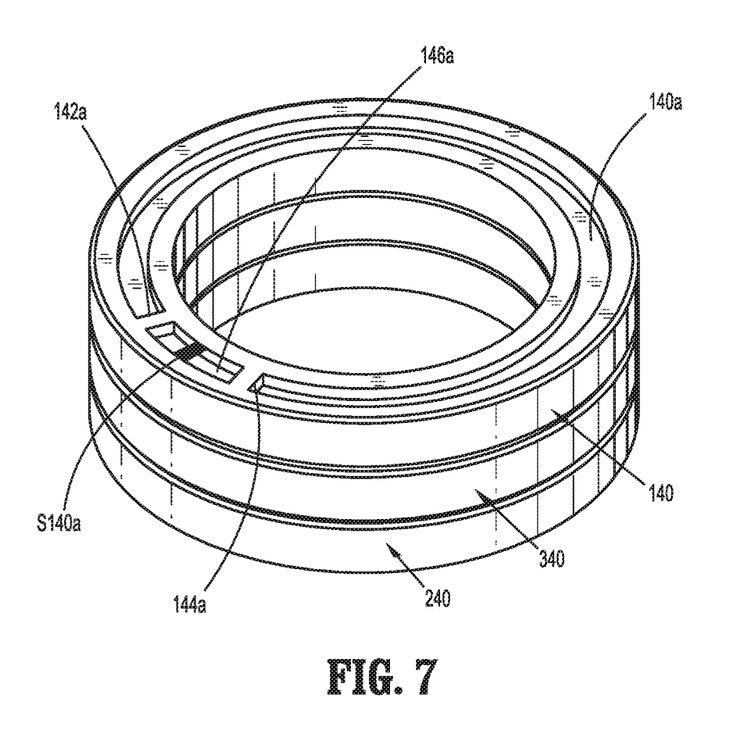
FIG. 7 is a perspective view of a series of annular members of another embodiment of a rotational position sensing system used with the instrument drive unit of FIG. 1.
Figure 8:
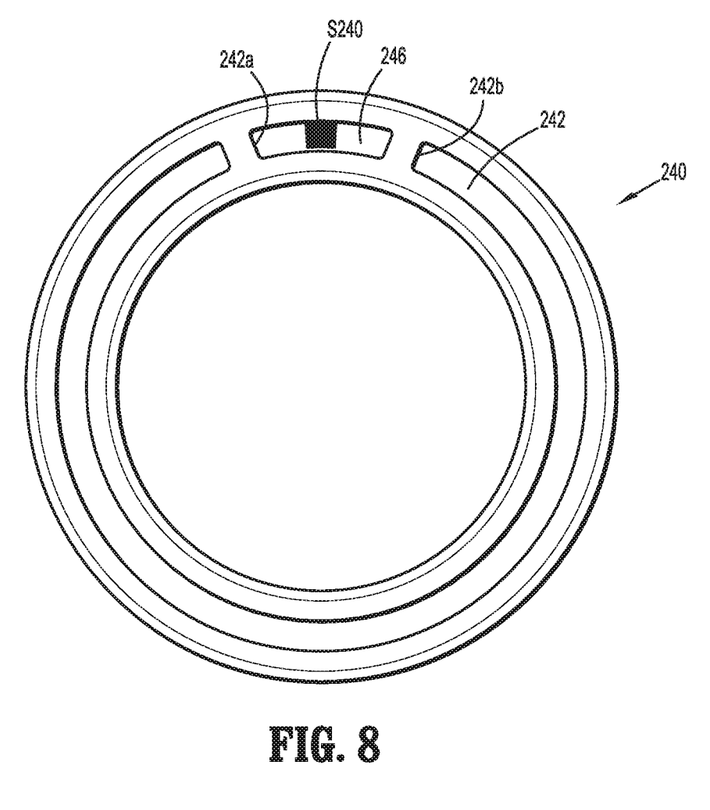
FIG. 8 is a bottom view of one of the series of annular members of FIG. 7.

With reference to FIGS. 7 and 8, the instrument drive unit 100 (FIG. 3) may include a plurality of annular members 140, 240, 340 in a stacked configuration. Having more than one annular member allows for an increased amount of rotation of the motor pack 122 relative to the hub 124. In some embodiments, more than three annular members may be provided. In embodiments, the motor pack 122 may rotate more than 720°. The second and third annular members 240, 340 are similar to the first annular member 140 and will therefore only described with the level of detail deemed necessary.

The second annular member 240 defines a lower annular channel 242 and includes a pair of stops 242a, 242b formed in the lower annular channel 242. The stops 242a, 242b are circumferentially spaced from one another to define a gap 246 therebetween. The second annular member 240 includes a sensor s240 disposed within gap 246. Sensor s240 of second annular member 240 is in communication with sensor s126 of hub 124 of instrument drive unit 100 and sensor s122 of motor pack 122 of instrument drive unit 100. In embodiments, the sensor s240 of second annular member 240 may be in communication with sensor s140b (FIG. 6) of lower annular channel 140b of annular member 140.

The third annular member 340 is disposed between the first and second annular members 140, 240. While not explicitly illustrated, the third annular member 340, like the first and second annular members 140, 240, may define upper and lower annular channels, and may include stops and sensors in each of its channels.

In operation, each of the annular members 140, 240, 340 is able to sense their rotational positions relative to one another due to the sensors associated with each. In addition, due to the interaction of the various stops of the annular members 140, 240, 340, a threshold amount of rotation of the motor pack 122 results in a rotation of the second annular member 240, a threshold amount of rotation of the second annular member 240 results in a rotation of the third annular member 340, and a threshold amount of rotation of the third annular member 340 results in a rotation of the first annular member 140.

As described above, after first annular member 140 achieves a threshold amount or degree of rotation relative to hub 124 (e.g., about 180° to about 360°), caused by the continued rotation of motor pack 122, one of the first pair of stops 142a, 144a of upper annular channel 140a of annular member 140 abuts surface feature 126 of hub 124 of instrument drive unit 100 causing annular member 140, and motor pack 122 with surgical instrument 10, to stop rotating. In this way, a continued actuation of motor "M" of surgical instrument holder 102 will fail to result in a rotation of motor pack 122, thereby preventing any damage from occurring to any components of surgical assembly 30 from the over-rotation of motor pack 122.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use with a robotic arm, the instrument drive unit comprising:
    an outer shell configured to be selectively coupled to a robotic arm; and
    an inner shell removably received within the outer shell and including:
        a hub non-rotatably received within the outer shell and having a distally extending surface feature;
        a motor pack including a proximal end rotatably coupled to the hub, and a surface feature extending proximally from the proximal end thereof; and
        at least one annular member defining:
            an upper annular channel having the surface feature of the hub received therein; and
            a lower annular channel having the surface feature of the motor pack received therein, the at least one annular member having a stop formed in each of the upper and lower annular channels, wherein upon the motor pack achieving a threshold amount of rotation relative to the hub, the surface feature of the motor pack abuts the stop of the lower annular channel to rotate the at least one annular member relative to the hub, and wherein upon the at least one annular member achieving a threshold amount of rotation relative to the hub, the stop of the upper annular channel abuts the surface feature of the hub stopping further rotation of the motor pack.

2. The instrument drive unit according to claim 1, wherein each of the proximal end of the motor pack, the at least one annular member, and the hub has a sensor in communication with one another and configured to sense the relative rotational positions of one another.

3. The instrument drive unit according to claim 2, wherein the sensor of the motor pack is disposed adjacent the surface feature thereof, the sensor of the at least one annular member is disposed adjacent the stop of the upper or lower annular channels, and the sensor of the hub is disposed adjacent the surface feature thereof.

4. The instrument drive unit according to claim 2, wherein at least one of the sensors of each of the motor pack, the at least one annular member, and the hub is at least one of a hall effect sensor, a rotary variable differential transformer, a variable reluctance sensor, a potentiometer, a capacitive rotary position sensor, an optical encoder, or a laser surface velocimeter.

5. The instrument drive unit according to claim 1, wherein the threshold amount of rotation of the motor pack relative to the hub is approximately 1 to 360 degrees, and the threshold amount of rotation of the at least one annular member relative to the hub is approximately 1 to 360 degrees, such that the motor pack is configured to rotate approximately 2 to 720 degrees relative to the outer shell.

6. The instrument drive unit according to claim 1, wherein the at least one annular member is a hollow ring having an H-shaped transverse cross sectional profile.

7. The instrument drive unit according to claim 1, wherein the surface feature of the motor pack is a curved projection slidably received within the lower annular channel of the at least one annular member, and wherein the surface feature of the hub is a curved projection slidably received within the upper annular channel of the at least one annular member.

8. A surgical assembly for use with and for selective connection to a robotic arm, the surgical assembly comprising:
 an instrument drive unit including:
  a hub having a surface feature;
  a motor pack having a surface feature and being rotatably coupled to the hub; and
  at least one annular member disposed between the hub and the motor pack, the at least one annular member defining:
   an upper annular channel; and
   a lower annular channel, the at least one annular member having a stop formed in each of the upper and lower annular channels, wherein upon the motor pack achieving a threshold amount of rotation relative to the hub, the surface feature of the motor pack abuts the stop of the lower annular channel to rotate the at least one annular member, and wherein upon the at least one annular member achieving a threshold amount of rotation relative to the hub, the stop of the upper annular channel abuts the surface feature of the hub stopping further rotation of the motor pack.

9. The surgical assembly according to claim 8, wherein the instrument drive unit further includes an outer shell, wherein the hub is non-rotatably received within the outer shell, the motor pack having a proximal end rotatably coupled to the hub.

10. The surgical assembly according to claim 9, wherein the surface feature of the hub extends distally from the hub, and the surface feature of the motor pack extends proximally from the proximal end thereof.

11. The surgical assembly according to claim 9, further comprising a surgical instrument holder including:
 a carriage housing having a first side configured for movable engagement to a surgical robotic arm, and a second side configured for non-rotatably supporting the outer shell of the instrument drive unit; and
 a motor disposed within the carriage housing and configured to effect rotation of the motor pack of the instrument drive unit.

12. The surgical assembly according to claim 11, wherein the surgical instrument holder further includes control circuitry disposed within the carriage housing and in communication with the motor and a sensor of each of the motor pack, the at least one annular member, and the hub, the control circuitry configured to stop operation of the motor upon the stop of the upper annular channel being disposed adjacent the surface feature of the hub.

13. The surgical assembly according to claim 8, wherein each of the motor pack, the at least one annular member, and the hub has a sensor in communication with one another and configured to sense the relative rotational positions of one another.

14. The surgical assembly according to claim 13, wherein the sensor of the motor pack is disposed adjacent the surface feature thereof, the sensor of the at least one annular member is disposed adjacent the stop of the upper or lower annular channels, and the sensor of the hub is disposed adjacent the surface feature thereof.

15. The surgical assembly according to claim 13, wherein at least one of the sensors of each of the motor pack, the at least one annular member, and the hub is at least one of a hall effect sensor, a rotary variable differential transformer, a variable reluctance sensor, a potentiometer, a capacitive rotary position sensor, an optical encoder, or a laser surface velocimeter.

16. The surgical assembly according to claim 8, wherein the threshold amount of rotation of the motor pack relative to the hub is approximately 1 to 360 degrees, and the threshold amount of rotation of the at least one annular member relative to the hub is approximately 1 to 360 degrees, such that the motor pack is configured to rotate approximately 2 to 720 degrees relative to the outer shell.

17. The surgical assembly according to claim 8, wherein the at least one annular member is a hollow ring having an H-shaped transverse cross sectional profile.

18. The surgical assembly according to claim 8, wherein the surface feature of the motor pack is a curved projection slidably received within the lower annular channel of the at least one annular member, and wherein the surface feature of the hub is a curved projection slidably received within the upper annular channel of the at least one annular member.

19. The surgical assembly according to claim 8, wherein the motor pack has a distal end configured to be non-rotatably coupled to a proximal end of an electromechanical instrument.

20. The surgical assembly according to claim 19, wherein the motor pack of the instrument drive unit is configured to actuate functions of the electromechanical instrument, and wherein the electromechanical instrument rotates with rotation of the motor pack of the instrument drive unit.

* * * * *